(12) United States Patent
Lynch et al.

(10) Patent No.: US 9,274,096 B2
(45) Date of Patent: Mar. 1, 2016

(54) ASSAY UTILISING CELLULAR BINARY HALF-ADDER SYSTEM

(71) Applicant: Manchester Metropolitan University, Manchester (GB)

(72) Inventors: Stephen Lynch, Cheshire (GB); Jon Borresen, Manchester (GB); Mark Slevin, Manchester (GB)

(73) Assignee: Manchester Metropolitan University, Manchester (GB)

( * ) Notice: Subject to any disclaimer, the term of this patent is extended or adjusted under 35 U.S.C. 154(b) by 0 days.

(21) Appl. No.: 14/230,511

(22) Filed: Mar. 31, 2014

(65) Prior Publication Data

US 2015/0276707 A1    Oct. 1, 2015

(51) Int. Cl.
*G01N 33/483* (2006.01)
(52) U.S. Cl.
CPC .................. *G01N 33/4836* (2013.01)
(58) Field of Classification Search
None
See application file for complete search history.

(56) References Cited

U.S. PATENT DOCUMENTS

| 5,664,211 | A | 9/1997 | Sobelman et al. |
| 6,581,046 | B1 | 6/2003 | Ahissar |
| 8,773,106 | B2 * | 7/2014 | Elder ........................... 324/71.1 |
| 8,928,353 | B2 * | 1/2015 | Lynch et al. .................... 326/52 |

FOREIGN PATENT DOCUMENTS

| GB | 876550 | 9/1961 |
| WO | 2012001372 | 1/2012 |

OTHER PUBLICATIONS

Huang J. et al. Neuronal Oscillations in Golgi Cells . . . Cerebellum 13(1)97-108, Feb. 2014.*

* cited by examiner

*Primary Examiner* — Ralph Gitomer
(74) *Attorney, Agent, or Firm* — Faegre Baker Daniels LLP

(57) ABSTRACT

An in vitro cell assay for detecting an effect a test condition has on one or more cells. The assay comprises providing a binary half-adder system comprising first and second oscillating cells, and detecting an effect a test condition has on the oscillation of said first and/or second cells.

27 Claims, 2 Drawing Sheets

ASSAY UTILISING CELLULAR BINARY HALF-ADDER SYSTEM

FIELD OF THE INVENTION

The present invention relates to in vitro cell assays which employ binary half-adder and/or other logic gates for use in studying an effect a test condition may have on the cells. In some embodiments, the cells are preferably neurons, or diseased neurons, in order to assay the effect a test condition may have on a neuron or diseased neuron.

BACKGROUND TO THE INVENTION

It is now understood that periodic behaviour is not confined to a limited number of physiological processes but is abundant in most biological systems. Periodicity in processes of the human body encompass phenomena such as genetic interactions, heartbeat rhythms, oscillating secretory, retina and muscle cells, cytoskeletal structures, bacterial oscillations, rhythmic oscillations (1-3). In 1952, whilst modelling neurons, Hodgkin and Huxley were able to accurately model the action potential in the giant squid axon (4). Their nonlinear ordinary differential equations approximate electrical characteristics of excitable oscillatory cells such as cardiomyocytes and neurons.

A number of research groups are now able to grow neurons on chips using a variety of techniques including an aligned micro-contact printing technique, patch clamping (which yields very accurate information but is invasive) and extracellular recordings by means of external micro-transducers or optical measurements (which are non-invasive) (5, 6), and it has recently been shown that Parkin diseased neurons can also be grown on a chip (7). In 2012 (8), it was shown that citicoline may be beneficial as a protective treatment against Alzheimer's following a stroke.

It is amongst the objects of the present invention to provide cell based assays which allow cells to be tested for an electrophysiological response to various stimuli. Such assays may be used in the testing of agents which may be of use in treating disease.

SUMMARY OF THE INVENTION

The present invention is based in part on the development of binary half-adder systems which comprise cells designed to act as oscillators, such that differences in any oscillatory pattern of a cell or cells in response to a stimuli can be detected. Creation of a binary half-adder using neurons which act as oscillators is described in US2013/0093458, which is hereby incorporated by reference in its entirety.

According to a first aspect of the invention there is provided an in vitro cell assay for detecting an effect a test condition has on one or more cells, the assay comprising:

providing a binary half-adder system comprising first and second oscillating cells; and detecting an effect a test condition has on the oscillation of said first and/or second cells.

Typically the cells are coated onto a surface, made of, for example, a glass or plastics material. Electrical contacts are located on the surface, the electrical contacts being wide enough at one end to allow them to be connected to an external electrical circuit (e.g. using electrical contact pins) and narrower at an opposite end where the cells are provided. The cells are connected by axons, dendrites or other equivalent connectors such that a binary half-adder is formed (as is described further below). The electrical contacts allow electrical or other suitable signals to be sent to inputs of the binary half-adder and allow output signals from the binary half-adder to be monitored. To retain the viability of the cells over a period of time, the cells may be coated or bathed by a suitable cell culture medium.

Thus, there may be provided a well or wells on the surface, within which the cells may be provided and into which the suitable culture medium and/or other agents may be added. The well may be sealable with an air-permeable membrane or cover which allows air and/or other gases to permeate into the well comprising the cells, but minimize loss of culture media from the well.

The assay further comprises subjecting the cells to a test condition, providing an input oscillatory signal to the binary half-adder system and detecting an output oscillatory signal from the binary half-adder system. The input and outputs of the binary half-adder system may be electrical signals. Alternatively, the input oscillatory signal may be other signals, capable of activating the oscillating cells.

A binary half-adder system requires an output to be low when two inputs are high. In an embodiment this is achieved by arranging the oscillating cells such that one of the oscillating cells has the ability to impart an inhibitory signal to another cell oscillator. In such an embodiment, oscillation of one oscillating cell prevents the other oscillating cell from oscillating.

Any cells which are capable of communicating with one another, for example by electrical signaling, may be employed in the present invention. Preferred cells include human or animal cells, such as human or animal neuronal cells, as well as cardiomyocytes and endothelial cells. If neuronal oscillating cells are utilised in the half-adder system, the communication may be by electrical signaling via axons and dendrites, for example. Alternatively, if cardiomyocytes are utilised, there may be direct physical communication between cells or any other suitable means of communication. The cells may be normal, diseased, or modified cells.

Normal cells are understood to be cells which have not been modified and are understood not to be diseased. This could include cells which may be induced to develop disease or be otherwise predisposed to becoming diseased.

Diseased cells may be cells which are associated with disease and may for example have been isolated from a subject suffering from a disease. For example, a diseased neuron may be obtained from a subject suffering from a neurodegenerative disease or disorder. A diseased cardiomyocyte may be obtained from a subject suffering from cardiovascular disease.

A modified cell may be a cell which has been genetically modified, for example, to overexpress or display reduced expression of a gene or protein and which may function to mimic a known disease or condition. A modified cell may also be a cell which has been subjected to conditions which are designed to mimic conditions which may be observed by diseased cells. For examples neurons may be subjected to hypoxic conditions in order to mimic a stroke, for example. Hypoxic conditions applied to cardiomyocytes may also serve to mimic ischaemia which can occur for example following cardiac infarction. This may be achieved by placing the cells in a reduced oxygen environment for a period of time, in order to mimic a hypoxic effect which may occur in vivo. Additionally, or alternatively, neurons may be subjected to conditions which invoke excitotoxicity. For example, neurons may be stimulated by neurotransmitters, such a glutamate and the like, which can cause the neurons to uptake high levels of calcium ions. This, can lead to pathological damage to the neurons and can be used to mimic conditions such as spinal injury, stroke, trauma to the brain, and neurodegenerative diseases. Additionally, or alternatively, protein or peptides known to be associated with certain diseases, such a prion proteins, Tau protein, amyloid beta and the like may be added to the cells in order to mimic certain disease conditions.

Cells which are modified to overexpress or display a reduced or no expression of a gene or protein associated with disease, can include the overexpression of proteins causatively involved in a neurodegenerative disease or disorder. For example, the protein may be a mutant of huntington protein, amyloid precursor protein (APP); alpha-synuclein (SNCA), insulin receptor substrate-1, or Tau protein, the expression of which are all associated with neurodegenerative disease.

The term "neurodegenerative disease or disorder" refers to a disease or a state characterized by a central nervous system (CNS) degeneration or alteration, especially in neurons, such as Alzheimer's disease (AD), Parkinson's disease (PD), Dementia with Lewy bodies (DLB), Frontotemporal dementia (FTD), Huntington's disease (HD) and amyotrophic lateral sclerosis (ALS).

In an embodiment, the oscillating cells are neuronal cells. The neuronal cells used to create the binary half-adder system may be excitatory or inhibitory cells (i.e. on their activating threshold being reached they may transmit excitatory or inhibitory signals). Oscillation of an inhibitory cell oscillator prevents oscillation of a connected cell oscillator.

In some embodiments of the invention the binary half-adder system is composed of neuronal cells and at least one of the neuronal cells is inhibitory. However, a variety of combinations of inhibitory and excitatory cells can be envisaged by the skilled person (see below for more detail).

In an embodiment, the system further comprises a third oscillating cell. In such an embodiment at least one oscillating cell is an inhibitory cell such that oscillation of the inhibitory cell prevents at least one other oscillating cell from oscillating. In one embodiment, the first and second oscillating cells are excitatory and the third oscillating cell is inhibitory. The skilled person would be well aware of how to identify excitatory and inhibitory neuronal cells. For example, neural cells can be predestined to be excitatory and inhibitory cells through treatment with chemicals such as GABA and gabazine, respectively, for example.

In embodiments where the oscillating cells are cardiomyocytes, endothelial cells or other suitable cells the inhibitory nature of at least one cell oscillator may be similarly provided by chemical treatment of the appropriate cells such that they are capable of providing a inhibitory signal to a second cell oscillator.

The binary half-adder may be used to monitor the effect the test condition has on one or more cells of the binary half-adder, by monitoring electrical outputs from the binary half-adder in response to electrical inputs. The term "test condition" may refer to application of a test agent, for example any agent whose effect on the cells in the cell culture, one is attempting to determine, or a particular cellular or environmental condition. The term "test agent" includes potentially active substances or substances known to be active for which one is attempting to test potential adverse or toxic effects. A test agent includes, but is not limited to, drugs, proteins, peptides, carbohydrates, nucleic acids, lipids, natural products, peptidomimetics, antibodies, small molecules and the like. The test agent may be added to the cells prior to, during and/or after the cells are used to form the binary half-adder.

The term "active substance" includes a substance which is able to prevent, repress or treat cellular dysfunctions, in particular those characterizing a neurodegenerative, cardiac or endothelial disease or disorder, including those characterizing an early stage of a neurodegenerative, cardiac or endothelial disease or disorder, as measured by oscillation or a pattern of oscillation of a cell or cells according to the invention. Alternatively, detection can be accompanied or complemented by the detection of other parameters, such as the morphology and the physiology of the cells, obtained for instance by microscopy. The term "adverse effect" includes an effect at the cellular level including a noxious cellular effect such as an abnormal increase or decrease in electrical activity parameters or abnormalities of cellular morphology, as measured by electrophysiological detection of the cells, optionally accompanied or complemented by the detection of other parameters, such as the morphology and the physiology, obtained for instance by microscopy or real-time imaging.

Alternatively, or in addition, the binary half-adder may be used to monitor the effect of physical damage or changes in cellular environment on cell functionality. For example, conditions of physical trauma, high and low temperature, or desiccation may be induced and the effect of such conditions determined. Detection includes any changes in oscillatory behavior of the cells and may be a comparison of diseased or modified cells to healthy wild-type normal cells. The assay may therefore further include providing an input oscillatory signal to the binary half-adder system and detecting an output oscillatory signal from the binary half-adder system prior to the step of subjecting the cells to a test condition, Changes in oscillatory behavior of the cells includes for example a change in an oscillatory signal which is required at an input of the binary half-adder in order to obtain an oscillatory signal at an output of the binary half-adder. The change of the input oscillatory signal may for example be a change in the amplitude and/or frequency of the input oscillatory signal. It also includes a change in an oscillatory signal which is seen at an output of the binary half-adder in response to an input oscillatory signal. The change of the oscillatory output signal may for example be a change in the amplitude and/or frequency of the output oscillatory signal. The change of the output signal may for example be the output signal ceasing to oscillate.

The changes in the input and/or output signals may for example be due to a change in action potential characteristics such as changes in frequency, amplitude, shape, spike kinetics, number of spikes, spike/firing rate, number of population burst, waveform, epoch, temporal correlation between action potentials measured by any pair of electrodes, in particular a decrease in the number of population bursts, a decrease in the total number of spikes a change in spike or burst characteristics such as spike or burst kinetics or intensity. Changes in chemical signaling within the cells (for example, the action of calcium and potassium channels) may result in changes in the characteristics of electrical signaling discussed above.

In addition to electrical inputs, the oscillatory cells may be activated using other signals which can activate the oscillating cells.

In some embodiments, the system may further include the concomitant measurement of biological outputs. The term "biological output" refers to any additional measurement of biological activity which could include for example, protein accumulation or degradation, changes in cellular appearance, changes in intercellular signaling etc. For example, when the oscillating cells are neuronal cells, further biological outputs may include protein accumulation (e.g. Tau, Huntington, APP, SNCA) calcium flux etc. A Tau-GFP reporter system could be utilised to determine Tau accumulation and this compared to the output of the binary half-adder. The use of biological outputs in combination with the outputs associated with the binary half-adder system allows the concomitant study and comparison of functional output with molecular and cellular characteristics. In a preferred embodiment the present invention is designed to allow for the in vitro testing of a test agent's potential to treat a particular disease or condition. The ability to test agents in vitro before they are administered to animals and/or man is very important and may allow considerable cost and/or time savings in the drug development process The term "treat" or "treating" refers to the capacity of obtaining a desired physiological effect. The effect may be prophylactic in terms of preventing or partially preventing a cellular dysfunction, and/or may be therapeutic in terms of a partial or complete cure of a cellular dysfunction by reversing an existing cellular dysfunction.

The cells of the present invention are detached and hence isolated from its parent organ and other organs. For example, neuronal cells may be dissociated from brain tissue by physical or chemical dispersion such by techniques described in "The neuron in tissue culture" L. Haynes, ed., Wiley and Sons 1999; ISBN: 0471975052 or Protocols for Neural Cell Culture, $2^{nd}$ ed (Fedorojf S. and Richardson A., eds; otowa, NJ: Humana Press. The skilled addressee is aware of how to isolate cells from other tissues (see for example reference 9). Suitable cell culture media are dependent on the cell type being studied and the skilled addressee is aware how to prepare and/or obtain such media from commercial sources. Media suitable for neuronal growth may include nutritive material such as amino acids, vitamins, minerals, glucose, albumin, insulin, transferrin, triiodo-L-thyronine, L-carnitine, ethanolamine, galactose, putrescine, corticosterone, linoleic acid, lipoic acid, progesterone, retinols, and antioxidants such as vitamin E, catalase, superoxide dismutase, and glutathione, (see Chen et al, 2008, J. Neurosci. Methods 171: 239-247), for example. In accordance with the invention, detection of an effect a stimuli may have on a cell or cells in the binary half-adder system may comprise a data processing step that can be implemented by a computer to analyse changes in oscillation characteristics of a cell or cells upon exposure to the stimuli. For example, a computer may apply input signals to inputs of the binary half-adder and compare the outputs to the outputs expected from a binary half-adder truth table.

Cellular activity is generally dependent on environmental conditions including temperature and pH, and as such detection typically takes place in an incubator compatible with the electronic hardware of the apparatus for recording oscillatory activity. In a particular embodiment the binary half-adder system for use in a method according to the invention may be stored in a container, such as a Petri dish to protect it from damage or contamination, in a temperature regulated storage incubator. The binary half-adder system may then be removed from the container and placed in an apparatus for recording oscillatory activity.

In a particular embodiment, the cells, such as neuronal cells are plated on a surface after coating the surface with a surface modifying agent such as polyethylenimine (e.g. 10 mg/ml) and laminin (e.g. 0.02 mg/ml) in Neurobasal medium or poly-L-lysine (0.01%) in water, which allows the attachment of cells and subsequent growth.

The binary half-adder is a building block which may be combined with other half-adders to form a full-adder (or other more complex circuits). For example, a binary full-adder may be formed using five neurons and associated axons/connections. For example, an appropriate binary full-adder configuration is shown and described in US2013/0093458. Other arrangements of neurons and axons may be used to form other circuits, for example using configurations shown and described in the above-incorporated US2013/0093458.

According to a second aspect of the invention there is provided an in vitro cell assay for detecting an effect a test condition on one or more cells, the assay comprising:

a) providing a logic gate comprising first and second oscillating cells; and b) detecting an effect a test condition has on the oscillation of said first and/or second cells.

The phrase "logic gate" may be interpreted as meaning a gate which provides a truth table of outputs in response to inputs, and includes for example a NOR gate, a NAND gate. Formation of a NOR gate and a NAND gate using oscillators is described and illustrated in US2013/009345.

The second aspect of the invention may include one or more features of the first aspect of the invention.

According to a third aspect of the invention there is provided a binary half-adder comprising three oscillatory cells, the first and second cells being excitatory and the third cell being inhibitory, the third cell being connected between the first and second cells such that oscillation of the second cell will cause oscillation of the third cell which will in turn inhibit oscillation of the first cell.

The term "oscillatory cell" may be interpreted as meaning a cell which oscillates when it receives an appropriate excitation (e.g. when it receives an oscillating input signal).

According to a fourth aspect of the invention there is provided a system comprising a binary half-adder comprising first and second oscillatory cells, and further comprising a monitoring apparatus connected to the binary half-adder by electrodes, wherein the monitoring apparatus is configured to apply input electrical signals to the binary half adder via the electrodes and to monitor for changes of electrical signals output from the binary half adder via the electrodes when a test condition is applied to the first and/or second oscillatory cells.

BRIEF DESCRIPTION OF THE DRAWINGS

The present invention will now be further described by way of example and with reference to the following figures in which.

DETAILED DESCRIPTION OF THE INVENTION

In summary, cells, such as neuronal cells (e.g. Cortical or hippocampal neurons; or clonal stem cells induced to differentiate into neurons) are cultured directly within a multi-electrode array (MEA) chamber in culture medium. The cells will migrate to electrodes of the array and will interconnect with one another using axons or other equivalent connectors such an dendrites. Many interconnections will be formed by the connectors. A binary half-adder is made by removing connectors that are not desired and thereby leave behind a connector arrangement which connects the cells as a binary half-adder. The unwanted connections can be removed by an operator using a needle or micro-laser observed through a microscope to displace those connectors.

Figure 1:
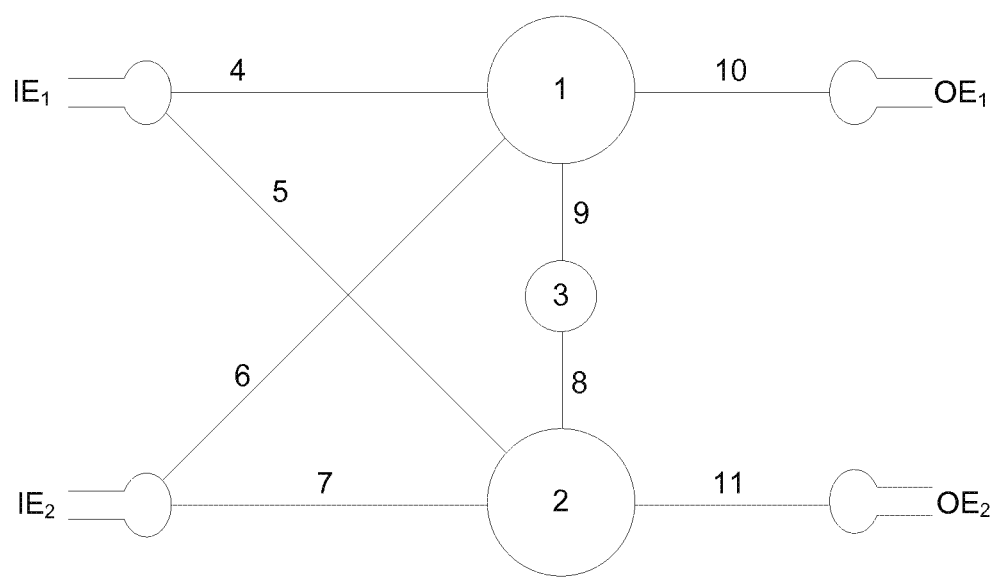
FIG. 1 represents schematically a binary half-adder formed using three neurons.

Referring to FIG. 1, the binary half-adder comprises three neurons 1-3. The first and second neurons 1,2 are excitatory (i.e. when they are oscillating they emit a signal which will excite oscillation in neurons to which they are connected).

The third neuron 3 is inhibitory (i.e. when it is oscillating it will emit a signal which will suppress oscillation in neuron 1 to which it is connected).

The neurons 1-3 are connected to input electrodes IE1, IE2 and output electrodes OE1, OE2 of the multi-electrode array. These connections can be made by dendrites 4, 5, 6, 7, axons 10, 11 or other equivalent connectors, or direct interaction between the cell body and the electrode. The electrodes may be coated with a biological solution such as geletin; prior to seeding the MEA with neural cells. On seeding the neural cells onto the MEA (using normal cell culture methods which will be well known to the skilled person) the neurons adhere to the underlying material and electrode substrate through normal adherent cell biology mechanisms. This could be via adherence of the cell body, axons, dendrites or any other appropriate cellular protrusion to the electrodes.

The input required for firing of the first neuron 1 is less than that required by the second neuron 2. This difference in threshold can result from a variety of factors including differing size of cell body, differing axonal diameter (with a larger diameter axon resulting in a lower threshold), differences in the concentration of chemicals used to define the neurons as excitatory or inhibitory etc. For example, the axon 10 which extends from neuron 1 may have a wider diameter than the axon 8 which extends from the second neuron 2. As a result of this difference in diameter, the resistance of the first axon 10 is lower than the resistance of the second axon 8. This difference in axon resistance affects the threshold of the neurons 1, 2 such that an oscillating signal at electrode IE1 of sufficient magnitude to excite the first neuron 1 to oscillate is not of sufficient magnitude to excite the second neuron 2. Similarly, an oscillating signal at input electrode IE2 of sufficient magnitude to excite the first neuron 1 to oscillate also not of sufficient magnitude to excite the second neuron 2.

However, the magnitude of the combination of oscillating signals applied at the first and second input electrodes IE1, IE2 will be sufficient to excite the second neuron 2 to oscillate. Thus, if the third neuron 3 were not present then an oscillating signal at either the first input electrode IE1 or the second input electrode IE2 would cause the first neuron 1 to oscillate, and an oscillating signal at both input electrodes would cause both the first neuron 1 and the second neuron 2 to oscillate.

The second neuron 2 is connected via an axon 8 to the third neuron 3, which in turn is connected by an axon 9 to the first neuron. When the second neuron 2 is oscillating it transmits an output signal along the axon 8 to the third neuron 3 which causes the third neuron to oscillate. Since the third neuron 3 is inhibitory, when it oscillates it emits a signal along the axon 9 which stops the first neuron 1 from oscillating.

Oscillation of the neurons 1, 2 generates output oscillating electrical signals which are carried by axon 10, 11 to the output electrodes OE1, OE2. Alternatively, the neural cell body can be directly attached to the output electrodes OE1, OE2 as discussed above.

Although axons 8 and 11 are depicted as separate axons in FIG. 1, it will be appreciated that they could be branches of the same axon (i.e. the neuron 2 may have a single axon output which splits into two branches).

The relationship between signals applied to the input electrodes IE1, IE2 and the signals seen at the output electrodes OE1, OE2 corresponds with the truth table of a binary half-adder (the neurons and axons form a binary half-adder):

| IE1 | IE2 | OE2 | OE1 |
|---|---|---|---|
| 0 | 0 | 0 | 0 |
| 0 | 1 | 0 | 1 |
| 1 | 0 | 0 | 1 |
| 1 | 1 | 1 | 0 |

The neurons are stimulated externally via the electrodes, e.g. using a computer to generate input oscillating signals of desired magnitudes. The signals emitted from the neurons and received at the output electrodes OE1, OE2 are monitored, e.g. using a computer. The computer may be considered to be an example of a monitoring apparatus. The monitoring apparatus, electrodes and binary half adder are together an example of a system configured to monitor for the effect of a test condition applied to the first and/or second oscillatory cells.

Figure 2A:
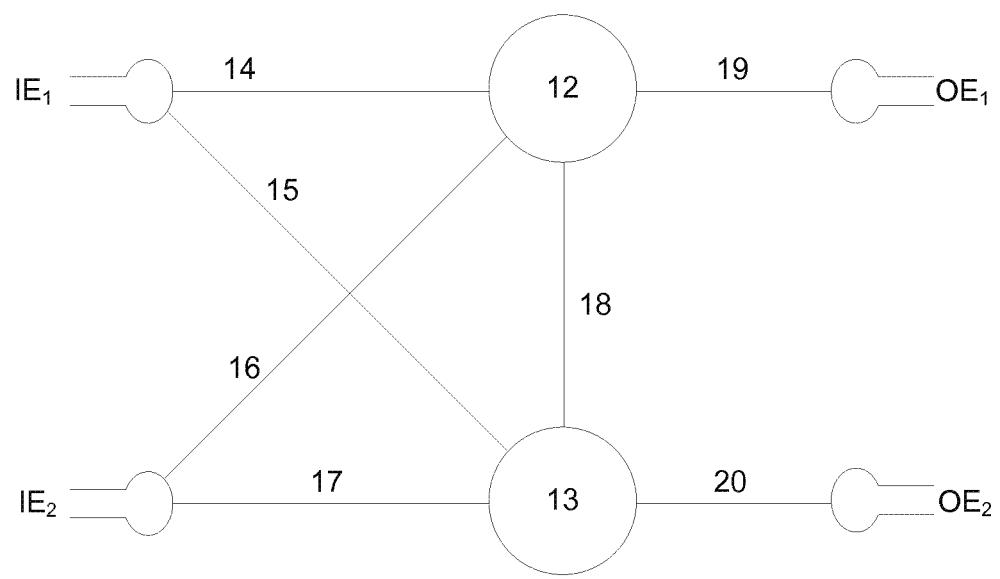
FIGS. 2A and 2B represent schematically binary half-adders formed using two neurons.
Figure 2B:
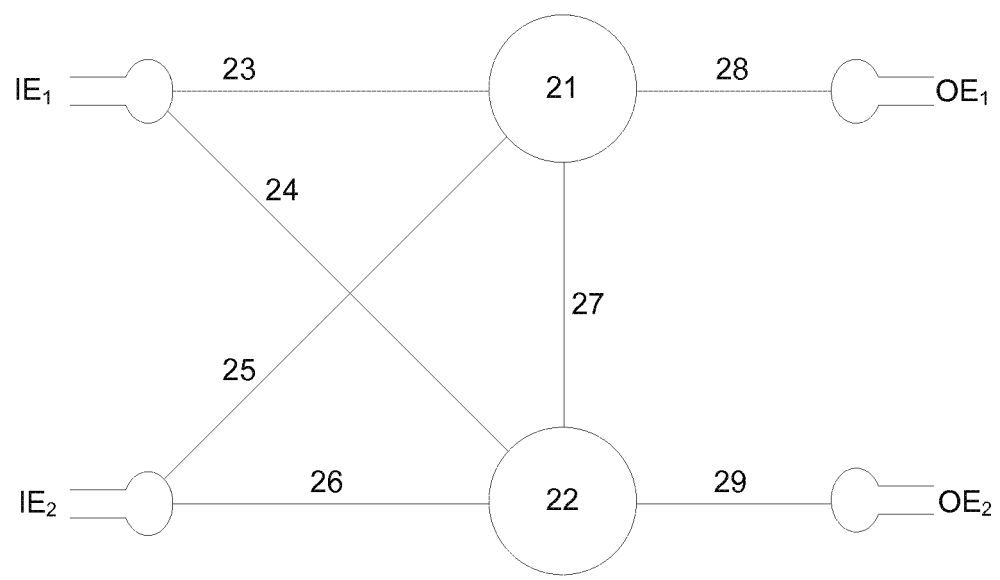

The neurons can be treated in test condition, with a test agent such as for example, pharmacological agents or toxins, or in a particular environmental condition, for example high or low temperature, and responses to these conditions and protective therapeutics measured. For example, the neurons may be monitored before during and after treatment with a test condition. Monitoring may include for example measuring the period of time following treatment before one of the neurons 1, 2 stops emitting an oscillating output. Physiological changes can be compared with biological responses measured concomitantly. Referring to FIGS. 2A and 2B, alternative binary half-adders are shown which are formed using two neurons. Rather than being composed of three neurons (two excitatory and one inhibitory) as in FIG. 1, FIG. 2A shows a binary half-adder formed from two neurons 12, 13. The first neuron 12 is excitatory (i.e. when it is oscillating it emits a signal which will excite oscillation in neurons to which it is connected). The second neuron 13 is inhibitory (i.e. when it is oscillating it will emit a signal which will suppress oscillation in neuron 12 to which it is connected).

The neurons 12, 13 are connected to input electrodes IE1, IE1 and output electrodes OE1, OE2 of the multi-electrode array. These connections can be made by dendrites 14, 15, 16, 17, axons 19, 20, other equivalent connectors, or direct interaction between the cell body and the electrode. As described above in relation to FIG. 1, the input required for firing of the first neuron 12 is less than that required by the second neuron 13. Consequently, an oscillating signal at electrode IE1 of sufficient magnitude to excite the first neuron 12 to oscillate is not of sufficient magnitude to excite the second neuron 13.

Similarly, an oscillating signal at input electrode IE2 of sufficient magnitude to excite the first neuron 12 to oscillate will not be of sufficient magnitude to excite the second neuron 13.

However, the magnitude of the combination of oscillating signals applied at the first and second input electrodes IE1, IE2 will be sufficient to excite the second neuron 13 to oscillate. The second neuron 13 is connected via an axon 18 to the first neuron 12. When the second neuron 13 is oscillating it transmits an inhibitory output signal along the axon 18 to the first neuron 12 which stops the first neuron 12 from oscillating.

Oscillation of the neurons 12, 13 generates output oscillating electrical signals which are carried to the output electrodes OE1, OE2 by axons 19, 20. Alternatively, the neural cell body can be directly attached to the output electrodes OE1, OE2 as discussed above, or via other equivalent connectors.

Although axons 18 and 20 are depicted as separate axons in FIG. 2A, it will be appreciated that they could be branches of the same axon.

FIG. 2B shows a binary half-adder also formed from two neurons 21, 22. Both first and second neurons 21, 22 are inhibitory (i.e. when they are oscillating they will emit a signal which will suppress oscillation in neurons to which they are connected).

As in the binary half-adders depicted in FIGS. 1 and 2A, the neurons 21, 22 of FIG. 2B are connected to input electrodes IE1, IE1 and output electrodes OE1, OE2 of the multi-electrode array. These connections can be made by dendrites 23, 24, 25, 26, axons 28, 29 or other equivalent connectors, or direct interaction between the cell body and the electrode. As described above in relation to FIGS. 1 and 2A, the input required for firing of the first neuron 21 is less than that required by the second neuron 22. Consequently, an oscillating signal at electrode IE1 of sufficient magnitude to excite the first neuron 21 to oscillate is not of sufficient magnitude to excite the second neuron 22.

Similarly, an oscillating signal at input electrode IE2 of sufficient magnitude to excite the first neuron 21 to oscillate is not of sufficient magnitude to excite the second neuron 22. However, the magnitude of the combination of oscillating signals applied at the first and second input electrodes IE1, IE2 will be sufficient to excite the second neuron 22 to oscillate. The second neuron 22 is connected via an axon 27 to the first neuron 21. When the second neuron 22 is oscillating it transmits an inhibitory output signal along the axon 27 to the first neuron 21 which stops the first neuron 21 from oscillating.

Oscillation of the neurons 21, 22 generates output oscillating electrical signals which are carried to the output electrodes OE1, OE2 by axons 28, 29. Alternatively, the neural cell body can be directly attached to the output electrodes OE1, OE2 as discussed above, or via other equivalent connectors.

Although axons 27 and 29 are depicted as separate axons in FIG. 2B, it will be appreciated that they could be branches of the same axon. Similarly, any depictions of binary half-adders in the Figures which indicate two axons leaving a single neuron may be branches of the same axon.

The binary half-adder is a building block which may be combined with other half-adders to form a full-adder (or other circuits). Using the technique described above a binary full-adder may be formed using five neurons and associated axons. An appropriate binary full-adder configuration is shown and described in US2013/0093458. Other arrangements of neurons and axons may be used to form other logic gates, for example using configurations shown and described in US2013/0093458.

In more detail the cells for use in the present invention can be obtained from commercial suppliers, such as Lonza, or can be obtained directly from tissue and isolated therefrom. For example, biopsies may be obtained from healthy and diseased individuals, and the appropriate cells isolated and grown in accordance with the present invention. This can allow a comparison to be made in response to stimuli provided to the cells and includes a stratified approach. It is not always possible to obtain cells in sufficient quantities, particularly if the cells are from brain tissue. Thus, cells which have been modified through genetic modification of by addition of proteins and/or other agents which are known to be associated with a particular disease or condition, can be added to the cells in order to mimic a disease or condition.

The isolated or purchased cells may initially be plated on a micro-electrode array substantially as described in Hales, C. M., Rolston, J. D., Potter, S. M. How to Culture, Record and Stimulate Neuronal Networks on Micro-electrode Arrays (MEAs). J. Vis. Exp. (39), e2056, doi:10.3791/2056 (2010), using multi-electrode arrays purchased from ALA Scientific Instruments (Farmingdale, N.Y., USA).

Once adhered to the substrate the cells may be allowed to grow in an appropriate medium. Neurons can be grown for example in a medium, such as Neurobasal A medium, obtained from Life Technologies (Paisley, UK). As explained further above, axons may be removed in order to leave behind connections between cells which together form a binary half-adder.

Test agents and/or other stimuli may be provided to the cells. For example, test agents at a variety of concentrations can be added to normal and diseased cells in order to see if the test agent has any effect on cellular oscillation. Additionally, the cells may be treated with agents and/or subjected to conditions designed to mimic certain diseases or conditions. For example, the binary half-adder system with the cells, may be transferred to an environment containing only 1% oxygen for a period of 4-24 hours, in order to mimic hypoxic conditions in a natural setting such as may be experienced following myocardial infarction or stroke, for example.

References

1. Rapp P. E. An atlas of cellular oscillators, J. Exp. Biology 1979; 81: 281-306.
2. Hierlemann A., Frey U., Hafizovic S., Heer F. Growing cells atop microelectronic chips: Interfacing electrogenic cells in vitro with CMOS-based microelectrode arrays introduction, Proc. of IEEE 2011; 99: 249-251.
3. Kruse K. and Jülicher F. Oscillations in cell biology, Opinion in Cell Biology 2005; 17: 20-26.
4. Hodgkin A. and Huxley A. A quantitative description of membrane current and its application to conduction and excitation in nerve, J. Physiol. 1952; 117: 500-544.
5. Delivopoulos E, Murray A F, MacLeod N. K. and Curtis J C. Guided growth of neurons and glia using microfabricated patterns of parylene-C on a silicon dioxide background, Biomaterials 2009; 30: 2048-2058.
6. Stephens C. L., Toda H., Palmer T. D. Adult neural progenitor cells reactivate superbursting in mature neural networks, Experimental Neurology 2012; 234: 20-30.
7. Jiang H B., Ren Y., Yuen E Y. Parkin controls dopamine utilization in human midbrain dopaminergic neurons derived from induced pluripotent stem cells, Nature Communications 2012; 3: Article number 668.
8. Krupinski J., Abudawood M., Matou-Nasri S. Citicoline induces angiogenesis improving survival of vascular/human brain microvessel endothelial cells through pathways involving ERK1/2 and insulin receptor substrate-1, Vascular Cell 2012; 4: 20.
9. Navone S E., Marfia G., Invernici G., Cristini S., Nava S., Balbi S., Sangiorgi S., Ciusani E., Bosutti A., Alessandri G., Slevin M., Parati E A. Isolation and expansion of human and mouse brain microvascular endothelial cells, Nature Protocols 2013: 8(9): 1680-93.

The invention claimed is:
1. An in vitro cell assay for detecting an effect a test agent has on one or more cells, the assay comprising:
providing a binary half-adder system comprising first and second oscillating cells; and
detecting an effect a test agent has on the oscillation of said first and/or second cells.

2. The assay of claim 1 wherein the detecting an effect a test agent has on the oscillation of said first and/or second cells further comprises:
  subjecting the cells to a test agent;
  providing an input oscillatory signal to the binary half-adder system; and
  detecting an output oscillatory signal from the binary-half adder system.

3. The assay of claim 2 wherein the assay further comprises the steps of:
  providing an input oscillatory signal to the binary half-adder system and detecting an output oscillatory signal from the binary half-adder system prior to the step of subjecting the cells to a test agent.

4. The assay of claim 1 wherein the second oscillating cell is an inhibitory cell such that oscillation of the second cell prevents the first cell from oscillating.

5. The assay of claim 1 wherein one or both of the cells are diseased or modified cells.

6. The assay of claim 1 wherein the cells are selected from the group consisting of neuronal cells, cardiomyocytes and endothelial cells.

7. The assay of claim 6 wherein the cells are neuronal cells.

8. The assay of claim 1 wherein the binary half-adder system further comprises a third oscillating cell.

9. The assay of claim 8 wherein at least one oscillating cell is an inhibitory cell such that oscillation of the inhibitory cell prevents at least one other oscillating cell from oscillating.

10. The assay of claim 1 wherein the test agent is a potentially active substance or a substance known to be active for which one is attempting to test potential adverse or toxic effects.

11. The assay of claim 1 wherein detecting an effect a test agent has on an oscillation of said first and/or second cells includes detecting changes in oscillatory behavior of the cells and may comprise a change in the input oscillatory signal or the output oscillatory signal.

12. The assay of claim 1 wherein the assay further comprises measurement of an additional biological output.

13. The assay of claim 10 wherein the additional biological output is protein accumulation or degradation.

14. An in vitro cell assay for detecting an effect physical trauma has on one or more cells, the assay comprising:
  providing a binary half-adder system comprising first and second oscillating cells; and
  detecting an effect physical trauma has on the oscillation of said first and/or second cells.

15. The assay of claim 14 wherein physical trauma is induced by hypoxia.

16. The assay of claim 14 wherein physical trauma is induced by desiccation.

17. The assay of claim 14 wherein the detecting an effect physical trauma has on the oscillation of said first and/or second cells further comprises:
  subjecting the cells to physical trauma;
  providing an input oscillatory signal to the binary half-adder system; and
  detecting an output oscillatory signal from the binary-half adder system.

18. The assay of claim 17 wherein the assay further comprises the steps of:
  providing an input oscillatory signal to the binary half-adder system and detecting an output oscillatory signal from the binary half-adder system prior to the step of subjecting the cells to physical trauma.

19. The assay of claim 14 wherein the second oscillating cell is an inhibitory cell such that oscillation of the second cell prevents the first cell from oscillating.

20. The assay of claim 14 wherein one or both of the cells are diseased or modified cells.

21. The assay of claim 14 wherein the cells are selected from the group consisting of neuronal cells, cardiomyocytes and endothelial cells.

22. The assay of claim 21 wherein the cells are neuronal cells.

23. The assay of claim 14 wherein the binary half-adder system further comprises a third oscillating cell.

24. The assay of claim 23 wherein at least one oscillating cell is an inhibitory cell such that oscillation of the inhibitory cell prevents at least one other oscillating cell from oscillating.

25. The assay of claim 14 wherein detecting an effect physical trauma has on an oscillation of said first and/or second cells includes detecting changes in oscillatory behavior of the cells and may comprise a change in the input oscillatory signal or the output oscillatory signal.

26. The assay of claim 14 wherein the assay further comprises measurement of an additional biological output.

27. The assay of claim 26 wherein the additional biological output is protein accumulation or degradation.

* * * * *